United States Patent
Toda et al.

(10) Patent No.: US 8,988,014 B2
(45) Date of Patent: Mar. 24, 2015

(54) WAKE-UP SYSTEM WITH COLOR TEMPERATURE CONTROL

(75) Inventors: Naohiro Toda, Kadoma (JP); Hiroki Noguchi, Kadoma (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 694 days.

(21) Appl. No.: 13/262,669

(22) PCT Filed: Apr. 21, 2010

(86) PCT No.: PCT/JP2010/057074
§ 371 (c)(1),
(2), (4) Date: Oct. 3, 2011

(87) PCT Pub. No.: WO2010/123031
PCT Pub. Date: Oct. 28, 2010

(65) Prior Publication Data
US 2012/0032616 A1 Feb. 9, 2012

(30) Foreign Application Priority Data
Apr. 23, 2009 (JP) .................... 2009-105299

(51) Int. Cl.
*H05B 37/02* (2006.01)
*A61M 21/00* (2006.01)
(Continued)

(52) U.S. Cl.
CPC .......... *A61M 21/00* (2013.01); *H05B 37/0227* (2013.01); *H05B 37/0281* (2013.01);
(Continued)

(58) Field of Classification Search
CPC ............. A61M 2021/0044; A61M 2021/0083; A61M 21/00; A61M 21/02; A61M 2205/18; H05B 37/0281; H05B 33/0854; H05B 33/0872; H05B 37/0227; G04G 11/00
USPC ......... 315/149, 152, 291, 294, 297, 360, 129; 368/244, 245, 250, 256, 73; 340/6.1, 340/10, 33, 575, 815.4
See application file for complete search history.

(56) References Cited

U.S. PATENT DOCUMENTS 5,327,331 A * 7/1994 Roberts .................. 362/176
8,436,556 B2 * 5/2013 Eisele et al. ............ 315/307
(Continued)

FOREIGN PATENT DOCUMENTS

JP 7-318670 12/1995
JP 11-135273 5/1999
(Continued)

OTHER PUBLICATIONS

Noguchi et al., "Improved Quality of Awakening by Simulating Dawn Lighting with an Ordinary Ceiling Light", Journal of the Illuminating Engineering Institute of Japan, vol. 85, No. 5, 2001, pp. 315-322.
(Continued)

*Primary Examiner* — Jimmy Vu
*Assistant Examiner* — Amy Yang
(74) *Attorney, Agent, or Firm* — Greenblum & Bernstein, P.L.C.

(57) ABSTRACT

A wake-up system includes an illumination apparatus and an interface apparatus. A wake-up time is input to the interface apparatus. The illumination apparatus varies output and color temperature of wake-up light that it irradiates. The output of the irradiated wake-up light is increased from a wake-up operation start time to the wake-up time. Color temperature of the wake-up light is controlled to become higher in one period than in another period between the wake-up operation start time to the wake-up time.

16 Claims, 7 Drawing Sheets

(51) Int. Cl.
*G04G 11/00* (2006.01)
*G04G 13/02* (2006.01)

(52) U.S. Cl.
CPC .................. *A61M2021/0044* (2013.01); *A61M 2021/0083* (2013.01); *A61M 2230/06* (2013.01); *A61M 2230/10* (2013.01); *A61M 2230/30* (2013.01); *A61M 2230/63* (2013.01); *G04G 11/00* (2013.01); *G04G 13/02* (2013.01)
USPC ................ 315/360; 315/129; 600/28; 600/26

(56) References Cited

U.S. PATENT DOCUMENTS

| 8,499,593 B2 * | 8/2013 | Van De Sluis et al. | ......... 68/256 |
| 2003/0095476 A1 * | 5/2003 | Mollicone et al. | ............ 368/250 |
| 2008/0103561 A1 * | 5/2008 | Moscovici | ...................... 607/88 |

FOREIGN PATENT DOCUMENTS

| JP | 2005-310438 | 11/2005 |
| JP | 2007-003499 | 1/2007 |
| JP | 2007-265804 | 10/2007 |
| JP | 2007265804 A | * 10/2007 |
| JP | 2008-010274 | 1/2008 |
| JP | 2008-310994 | 12/2008 |

OTHER PUBLICATIONS

Kruithof, "Tubular Luminescence Lamps for General Illumination", Philips Technical Review, vol. 6, No. 3, Mar. 1941, pp. 65-96.

Moseley et al., "Light transmission through the human eyelid: in vivo measurement", Ophthalmic and Physiological Optics, vol. 8, No. 2, Apr. 1988, pp. 229-230.

* cited by examiner

WAKE-UP SYSTEM WITH COLOR TEMPERATURE CONTROL

TECHNICAL FIELD

The present invention relates to a wake-up system which promotes wake-up of a sleeper by irradiating a wake-up light and a control method of an illumination apparatus used for the wake-up system.

BACKGROUND ART

As for a wake-up system which promotes wake-up of a sleeper by irradiating a wake-up light, a wake-up system that increases output (power, brightness or luminance) of a wake-up light gradually toward a wake-up time, and thereby, awakes a sleeper at the wake-up time is conventionally known (see, for example, JP Hei 7-318670 A, JP 2007-003499 A, or Noguchi Hiroki et al. "Improvement of Wake-up by Irradiation of Gradually Increased Light Before Wake-up Using A Ceiling Illumination", Journal of the Illuminating Engineering Institute of Japan, 2001, 85 (5), pp. 315-322). In such a wake-up system, when an incandescent lamp is used as a light source, for example, color temperature of the wake-up light is higher in a state that the output of the wake-up light is smaller, and the color temperature of the wake-up light is lower in a state that the output of the wake-up light is larger.

Generally, in a low illumination state where output of light from a light source is smaller, a person feels comfortable when color temperature of the light source is lower, but the person feels uncomfortable when the color temperature of the light source is higher. Alternatively, in a high illumination state where the output of light from the light source is larger, the person feels comfortable when color temperature of the light source is higher but the person feels uncomfortable when color temperature of the light source is lower. (see Kruithof, A. A., "Tubular luminescence lamps for general illumination," Philips Technical Review, 1941, 6, pp. 65-96). Therefore, in the wake-up system, if the color temperature of the light source is higher when the output of the wake-up light is smaller or the color temperature of the light source is lower when the output of the wake-up light is larger, as mentioned above, there is a fear that the sleeper feels uncomfortable at any time when he/she awakes.

DISCLOSURE OF INVENTION

The present invention is conceived to solve the above mentioned conventional problems and purposed to provide a wake-up system which enables to bring comfortable wake-up to a sleeper even when the sleeper awakes as any time in the wake-up system that promotes wake-up of the sleeper by irradiating wake-up light and by increasing power of the wake-up light gradually.

A wake-up system in accordance with an aspect of the present invention comprises an illumination apparatus which irradiates wake-up light, a control apparatus which controls output of the wake-up light irradiated from the illumination apparatus, and an interface apparatus which is operated by a user to input at least a wake-up time, characterized by that the illumination apparatus comprises an output variation apparatus which varies output of the wake-up light to be irradiated, and a color temperature variation apparatus which varies color temperature of the wake-up light, and the control apparatus comprises a light output control unit which controls the output variation apparatus so as to increase the output of the wake-up light irradiated from the illumination apparatus from an wake-up operation start time to the wake-up time, and a color temperature control unit which controls the color temperature variation apparatus such that the color temperature of the wake-up light in a time period from a first time, which is a time passing a first predetermined time period from the wake-up operation start time, to the wake-up time becomes higher than the color temperature of the wake-up light in a time period from a second time, which is a time before a second predetermined time period shorter than the first predetermined time period from the first time, to the first time.

On the other hand, a control method of an illumination apparatus in accordance with an aspect of the present invention is the control method of the illumination apparatus used in the wake-up system to promote wake-up of a sleeper by irradiation of wake-up light, characterized by increasing output of the wake-up light irradiated from the illumination apparatus from a wake-up operation start time toward a wake-up time, and increasing color temperature of the illumination apparatus such that the color temperature of the wake-up light in a time period from a first time, which is a time passing a first predetermined time period from the wake-up operation start time, to the wake-up time becomes higher than the color temperature of the wake-up light in a time period from a second time, which is a time before a second predetermined time period shorter than the first predetermined time period from the first time, to the first time.

According to such a configuration, the color temperature becomes lower when the output of the wake-up light is smaller and the color temperature becomes higher when the output of the wake-up light is larger, so that a relation between the light output and the color temperature of the wake-up light becomes comfortable to the sleeper to be irradiated by the wake-up light, and thus, even when the sleeper awakes at any time, it can bring the comfortable wake-up to the sleeper.

MODE FOR CARRYING OUT THE INVENTION

Figure 1:
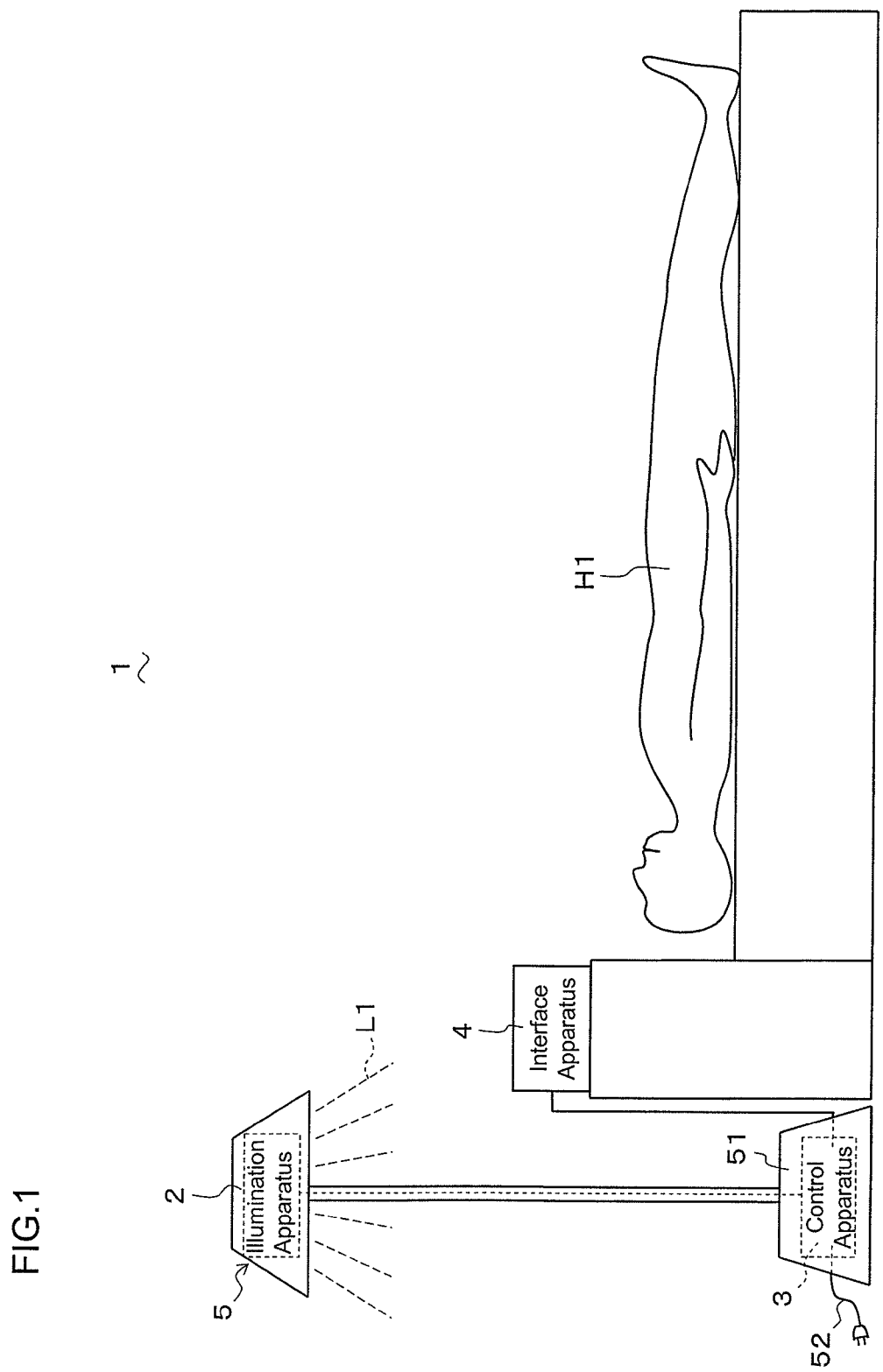
FIG. 1 is a view showing a configuration of a wake-up system in accordance with an embodiment of the present invention.

A wake-up system and a control method of an illumination apparatus used for the same in accordance with an embodiment of the present invention are described with reference to the drawings. FIG. 1 shows a configuration of a wake-up system in accordance with this embodiment. This wake-up system 1 comprises an illumination apparatus (a light source) 2 which irradiates a wake-up light L1, a control apparatus 3 which controls the illumination apparatus 2 so as to vary output and color temperature of the wake-up light L1, and an interface apparatus (an operation panel or a remote control device) 4 which is operated by a user to input or set various control conditions by the control apparatus 3.

In this wake-up system 1, it is possible to vary the output and the color temperature of the wake-up light L1 irradiated from the illumination apparatus 2, and the control apparatus 3 controls the illumination apparatus 2 such that the output of the wake-up light L1 is gradually increased from start of irradiation of the wake-up light L1 by the illumination apparatus 2, the color temperature of the wake-up light L1 is made lower in a stage that the output of the wake-up light L1 is smaller, and the color temperature of the wake-up light L1 is made gradually higher corresponding to the increase of the output of the wake-up light L1. Thereby, when a user awakes, it enables natural wake-up without feeling uncomfortable. Hereupon, the above mentioned control operation of the illumination apparatus 2 by the control apparatus 3 is called wake-up operation. The interface apparatus 4 is an operation apparatus comprising an input unit such as operation buttons and a display unit such as a liquid crystal display device (including a touch panel that displays operation buttons as images on a display screen), for example, and used to input and display a wake-up operation start time at which the wake-up operation is started, and a wake-up time (that is uprising time) at which the user is awaken, which is later than the start time, temporally.

In the example of configuration shown in FIG. 1, the illumination apparatus 2 is installed on a floor lamp 5 and the control apparatus 3 is accommodated in a pedestal 51 of the floor lamp 5. In addition, the interface apparatus 4 is established separately from the floor lamp 5. The illumination apparatus 2 and the interface apparatus 4 are respectively connected to the control apparatus 3 by cables, and a power strip 52 is drawn from the control apparatus 3. In addition, the configuration of the wake-up system 1 is not limited to this, and the illumination-apparatus 2 may be installed on a stand having a short arm such as a desk stands. Alternatively, the illumination apparatus 2 may be a ceiling light type or a pendant light type illumination apparatus installed on a ceiling for illuminating entirely, or a an illumination apparatus for illuminating partially such as a down light installed on the ceiling. Furthermore, establishment places of the control apparatus 3 and the interface apparatus 4 are not limited in particular, and they may be other places. Still furthermore, the illumination apparatus 2 and the interface apparatus 4 may be connected to the control apparatus 3 via wireless communication. As for the wireless communication means, infrared rays, specific low-power radio, Bluetooth, or the like can be used.

Figure 2:
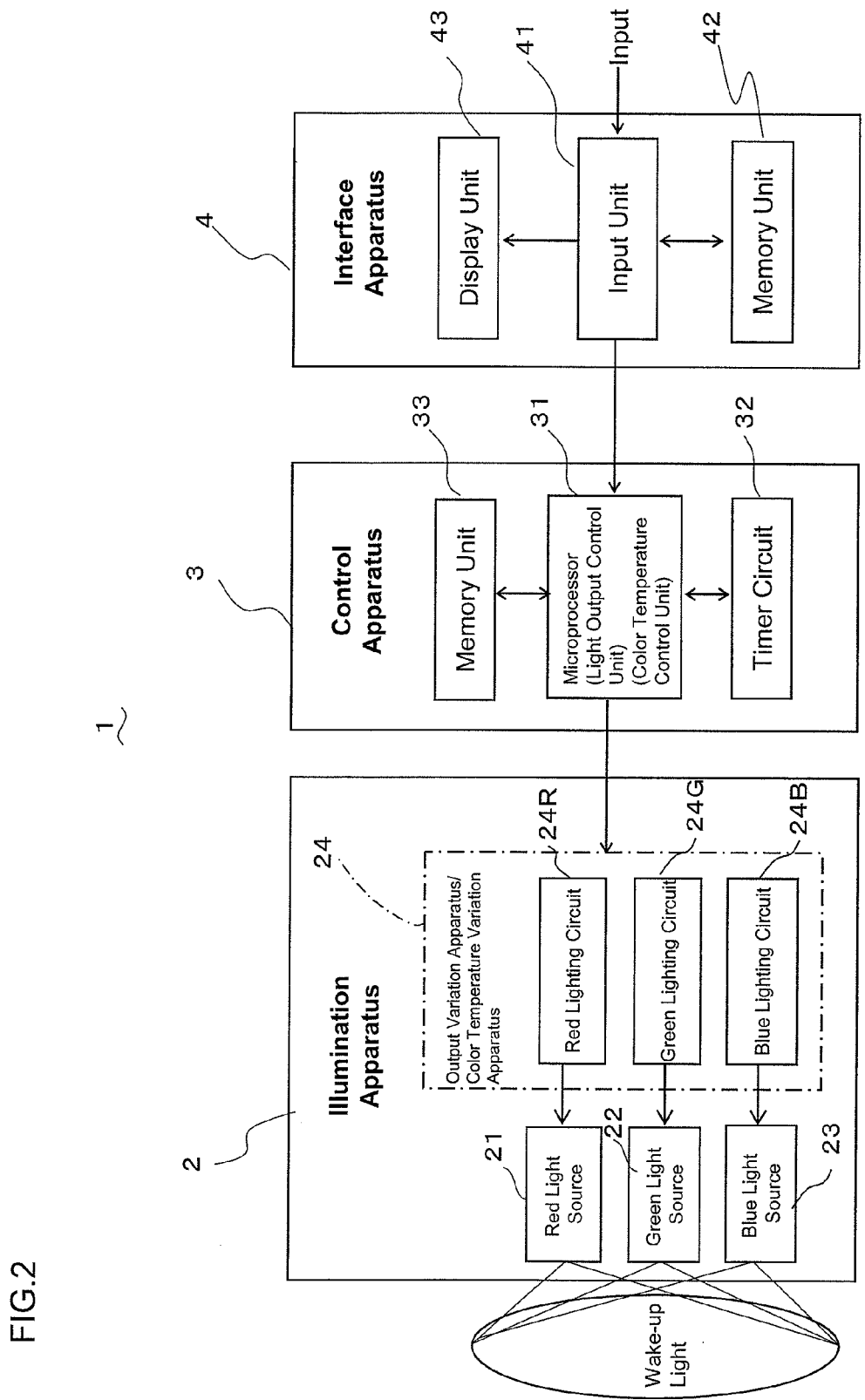
FIG. 2 is a block diagram showing a configuration of the above mentioned wake-up system.

FIG. 2 shows a block configuration of the wake-up system. The illumination apparatus 2 comprises a red light source 21 which emits red light, a green light source 22 which emits green light, a blue light source 23 which emits blue light, a red lighting circuit 24R, a green lighting circuit 24G and a blue lighting circuit 24B which control lighting of respective light sources 21 to 23 individually. Each of the light sources 21 to 23 is configured by combination of elements included in the same kind or elements included in different kinds among the elements such as light emitting diode (LED), organic electroluminescence (organic EL), inorganic electroluminescence (inorganic EL). In this example of configuration, a synthesized light of lights emitted from respective light sources 21 to 23 is outputted from the illumination apparatus 2 as the wake-up light L1. By controlling the outputs of the light sources 21 to 23 by the lighting circuits 24R, 24G and 24B individually, the output and the color temperature of the wake-up light L1 can be varied simultaneously. In other words, the lighting circuits 24R, 24G and 24B serve as an output variable apparatus and a color temperature variable apparatus 24 of the wake-up light L1.

The control apparatus 3 comprises a microprocessor 31 which performs the wake-up operation by controlling the driving of the lighting circuits 24R, 24G and 24b, a timer circuit 32 for counting timings of various motion in the wake-up operation, and a memory unit 33 which memorizes programs and control patterns for performing the wake-up operation. The microprocessor 31 receives information of the wake-up operation start time and the wake-up time outputted from the interface apparatus 4, counts current time by the timer circuit 32, and starts the wake-up operation when the current time reaches to the wake-up operation start time. In addition, the microprocessor 31 calculates time from the wake-up operation start time to the wake-up time by the timer circuit 32 and coordinates detail of the wake-up operation corresponding to the time. The interface apparatus 4 has an input unit 41 such as operation buttons, volumes, or a touch panel by which a user inputs the wake-up operation start time and the wake-up time, a memory unit 42 which memorizes various times inputted through the input unit 41, and a display unit 43 that display input information such as the wake-up operation start time and the wake-up time inputted through the input unit 41, and transmits those various information to the control apparatus 3. The microprocessor 31 serves as a light output control unit that controls each of the lighting circuits 24R, 24G and 24B (the output variation apparatus) to vary the output of the wake-up light L1 irradiated from the illumination apparatus 2 during the wake-up operation, and a color temperature control unit that controls each of the lighting circuits 24R, 24G and 24B (the color temperature variation apparatus) to vary the color temperature of the wake-up light during the wake-up operation.

The interface apparatus 4 is not necessarily provided separately from the control apparatus 3, and both may be integrated for one body. In that case, a single memory can be used commonly for the memory unit 33 and the memory unit 42. Furthermore, the illumination apparatus 2, the control apparatus 3 and the interface apparatus 4 may be integrated for one body. Still furthermore, a timer circuit may be built into the illumination apparatus 2 or the interface apparatus 4, too. Still furthermore, it may be constituted that two-way communication is allowed between the control apparatus 3 and the interface apparatus 4, and the current time, the time from the current time to the wake-up operation start time and/or a remaining time to the wake-up time, and an elapsed time from the wake-up operation start time to the wake-up time which are transmitted from the control apparatus 3 are displayed on the display unit 43 of the interface apparatus 4.

Figure 3:
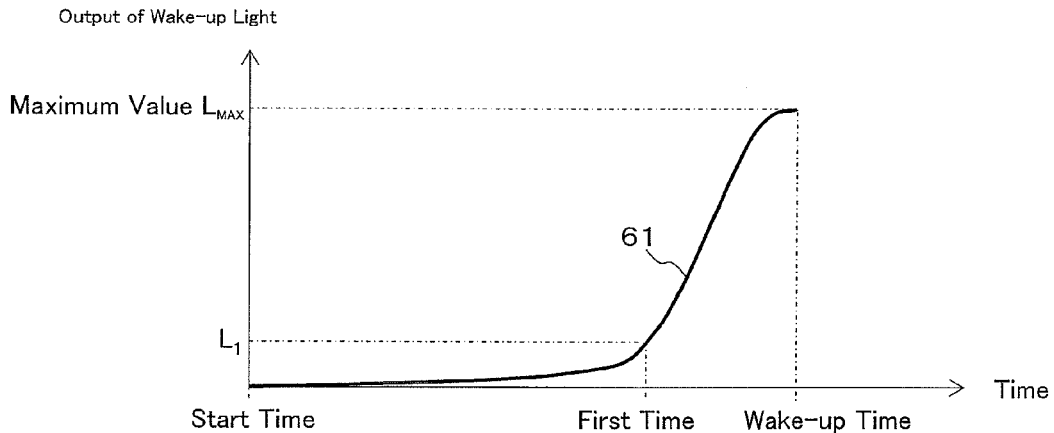
FIG. 3 is a graph showing an example of output characteristics of a wake-up light in the above mentioned wake-up system.

FIG. 3 shows output characteristics 61 of the wake-up light L1 irradiated from the illumination apparatus 2 which is controlled by the control apparatus 3. As shown in FIG. 3, in the output characteristics 61 of the wake-up light L1, the output of the wake-up light L1 at the wake-up operation start time (in the figure, it is shown as "start time") is substantially zero (1×), gently increases as time go on, and suddenly increases after passing a first predetermined time T1, that is, after a first time. Subsequently, the output of the wake-up light L1 becomes the maximum value $L_{MAX}$ at the wake-up time. Hereupon, the time at which the output of the wake-up light L1 suddenly increases or a time at which the output of the wake-up light L1 reaches to a predetermined value $C_1$ is called the first time. The first time is calculated by that a value which is obtained by multiplying a predetermined rate to the time period from the wake-up operation start time to the wake-up time is subtracted from the wake-up time or added to the wake-up operation start time. By such a calculation, the first time is previously set at the time when the wake-up operation start time and the wake-up time are inputted by the user.

The time period from the wake-up operation start time to the first time is in preparation of wake-up and it is disinclined to awake the user H1 while sleeping, and the time period from the first time to the wake-up time during which the user H1 may awake at any time. By way of an example, the output of the wake-up light L1 at the first time is set to be equal to or smaller that 40 (1×), preferably, larger than 0 (1×) and equal to or smaller than 23 (1×), for example, in conversion to illuminance on a face of the user H1. In addition, the maximum value $L_{MAX}$ of the output of the wake-up light L1 is set to be equal to or larger than 100 (1×), preferably, equal to or larger than 200 (1×), for example, in conversion to illuminance on the face of the user H1. The output of the wake-up light L1 might become smaller than a targeted value caused by change of circumference environment, temperature change of each of the light sources 21 to 23 or the lighting circuit 24. Even in such a situation, when reduction of illuminance on the face of the user H1 is in a degree of several (1×), there is no problem in particular. In addition, the time when the output of the wake-up light L1 becomes the largest is not necessarily the wake-up time, and it may be former a little from the wake-up time.

Figure 4:
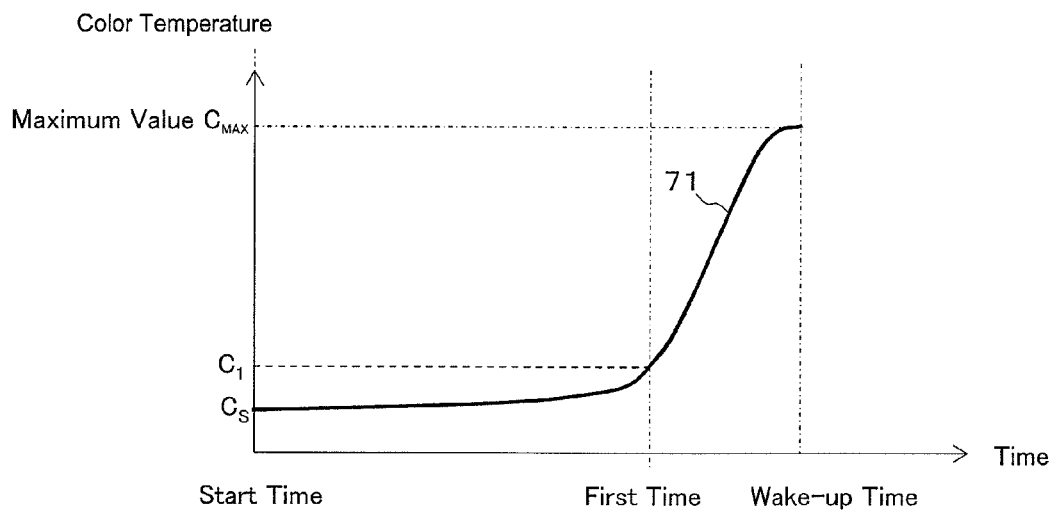
FIG. 4 is a graph showing an example of color temperature characteristics of the wake-up light in the above mentioned wake-up system.
Figure 5:
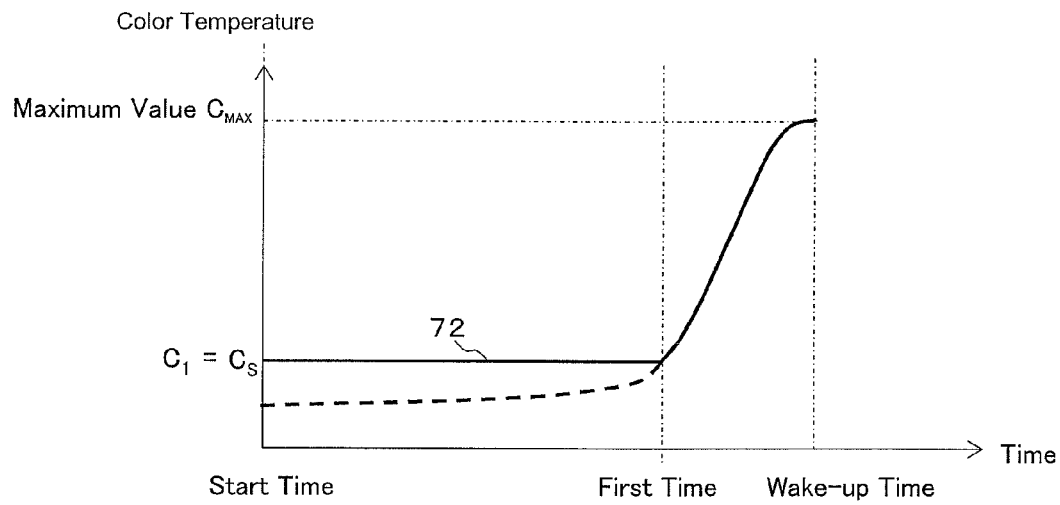
FIG. 5 is a graph showing another example of color temperature characteristics of the wake-up light.

FIG. 4 and FIG. 5 respectively show color temperature characteristics 71, 72 of the wake-up light L1. In the color temperature characteristics 71 of the wake-up light L1 shown in FIG. 4, the color temperature of the wake-up light L1 gently rises with progress of time from the wake-up operation start time and suddenly rises towards a maximum power time (at the awake-up time in this embodiment) from the first time, and it becomes the maximum value $C_{MAX}$ at the maximum power time of the wake-up light L1 ($C_S<C_1<C_{MAX}$). On the other hand, in the color temperature characteristics 72 shown in FIG. 5, in a time period from the wake-up operation start time to the first time, the color temperature of the wake-up light L1 is approximately constant ($C_S=C_1<C_{MAX}$).

By way of an example, the color temperature $C_1$ of the wake-up light L1 at the first time is set to be equal to or smaller than 4000 K, preferably, equal to or smaller than 3000 K. In addition, the maximum value of the color temperature $C_{MAX}$ of the wake-up light L1 is set to be equal to or larger than 5000 K which is the color temperature of white light, preferably, equal to or larger than 6000 K which is the color temperature of sunlight. The time at which the color temperature of the wake-up light L1 becomes the highest is not necessarily the maximum power time of the wake-up light L1, and it may be former a little from the time. In case that the maximum power time at which the output of the wake-up light L1 has the maximum value is former from the wake-up time, a time at which the color temperature of the wake-up light L1 becomes the highest may be the wake-up time.

The control patterns shown in FIG. 3 and FIG. 4 or FIG. 3C (SIC: correctly, it should be FIG. 5) are merely examples, and the control pattern of the illumination apparatus 2 is not limited to these. For example, it may be configured that a plurality of different control patterns are memorized in the memory unit 33 of the control apparatus 3, and the user can select an optional control pattern by operating the input unit 41 of the interface apparatus 4. In addition, it may be configured that a plurality of output characteristics and color temperature characteristics of the wake-up light L1 is memorized in the memory unit 33 individually, and the output characteristics and the color temperature characteristics are optionally combined. The control apparatus 3 controls the output and the color temperature of the wake-up light L1 to enable to reproduce the output characteristics and color temperature characteristics selected by the user.

Furthermore, it may be configured that various kinds of sensors for detecting living body information such as movement of human body, pulsation, heartbeat, blood pressure, brain waves of the user H1 while sleeping in this wake-up system 1 are provided, and the control apparatus 3 selects and performs a suitable one among a plurality of control patterns automatically, on the basis of the measurement results by the sensors. Alternatively, it may be configured that the outputs and the color temperatures of the wake-up light L1 at a plurality of times such as the wake-up operation start time, the first time and the wake-up time are memorized in the memory unit 33, and inclinations of the output characteristics and the color temperature characteristics are varied corresponding to the wake-up operation start time and the wake-up time set by the user H1. Furthermore, it may be configured that an illumination sensor and a color temperature sensor are provided on the interface apparatus 4, and an illuminance and a color temperature due to the wake-up light L1 irradiated from the illumination apparatus 2 are actually measured so as to perform feedback control by the control apparatus 3.

In this way, in the wake-up system 1 in accordance with this embodiment, in the time period from the wake-up operation start time to the first time, the output of the wake-up light L1 is gradually increased in a first inclination as time go on, and the color temperature of the wake-up light L1 is gradually increased in a second inclination simultaneously, and in the time period from the first time to the wake-up time or the time at which the output of the wake-up light becomes the maximum, the output of the wake-up light L1 is suddenly increased in a third inclination larger than the first inclination as time go on, and the color temperature of the wake-up light L1 is suddenly increased in a fourth inclination larger than the second inclination simultaneously. Consequently, the illumination apparatus 2 can be controlled such that while the output of the wake-up light L1 is smaller, the color temperature of the wake-up light L1 is lower simultaneously, and while the output of the wake-up light L1 is larger, the color temperature of the wake-up light L1 is higher simultaneously. By the way, as mentioned above, it is known that in the low illumination state where the output of light from the light source is smaller, a person feels comfortable when the color temperature of the light source is lower, but the person feels uncomfortable when the color temperature of the light source is higher. Therefore, in case of using this wake-up system 1, even the user H1 awakes at any time, it is possible to give comfortable wake-up to the user H1.

Still furthermore, the term "inclination" mentioned here means a rate of increase of the output of the wake-up light L1 or a rate of climb of the color temperature of the wake-up light L1 per unit time. These first to fourth inclinations are not necessarily constant respectively, and they may be linear or non-linear if they increase or climb in monotonous. In addition, when the inclination is varied in the time period from the wake-up operation start time to the first time and in the time period from the first time to the wake-up time or the maximum power time of the wake-up light, it may be a mean value or the maximum value.

Figure 6:
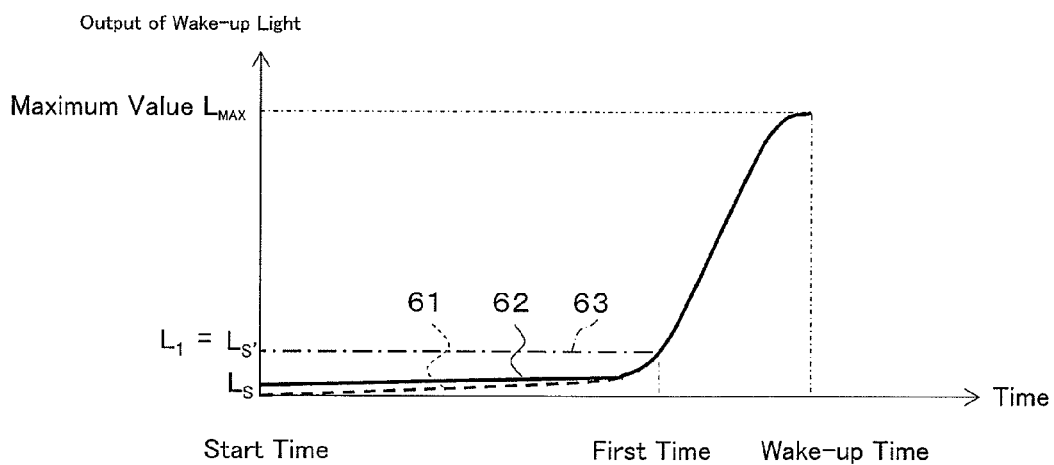
FIG. 6 is a graph showing another example of output characteristics of the wake-up light.

Still furthermore, when a discharge lamp such as a fluorescent lamp is used as a light source, it is difficult to increase the output from a state of almost "0" gradually. Alternatively, when LEDs are used as light sources, it is difficult to uniform the outputs of all the LED elements in a predetermined level in low output due to variation of leakage current characteristics of individual LED elements. Therefore, it is possible to configure that the output of the wake-up light L1 has a constant value larger than "0" at the wake-up operation start time like the output characteristics 62 shown by solid line in FIG. 6, for example. An initial value $L_S$ of the output of the wake-up light L1 at the wake-up operation start time may be lower than the output value $L_1$ of the wake-up light L1 at the first time, and be increased gradually. Alternatively, the output of the wake-up light L1 may be a constant value $L_{S'}$ from the wake-up operation start time to an optional time before the first time like output characteristics 63 shown by one dotted chain line in FIG. 6. In addition, the output characteristics 61 in FIG. 3 are shown by dotted line in FIG. 6 as a comparative example.

By the way, according to Moseley, M. J. et al., "Light transmission through the human eyelid: in vivo measurement," Ophthalmic Physiol Opt., 1988, 8 (2), pp. 229-30, a light having a wavelength in a short wavelength area around 580 nm or shorter than it cannot transmit eyelid, so that one rarely feels the light of short wavelength while closing eyes. Therefore, if illuminance on a face of the user H1 is in the same level, a light of higher color temperature which contains a large amount of short wavelength ingredients and a small amount of long wavelength ingredients is difficult to transmit eyelid than a light of lower color temperature which includes a small amount of short wavelength ingredients and a large amount of long wavelength ingredients.

Figure 7:
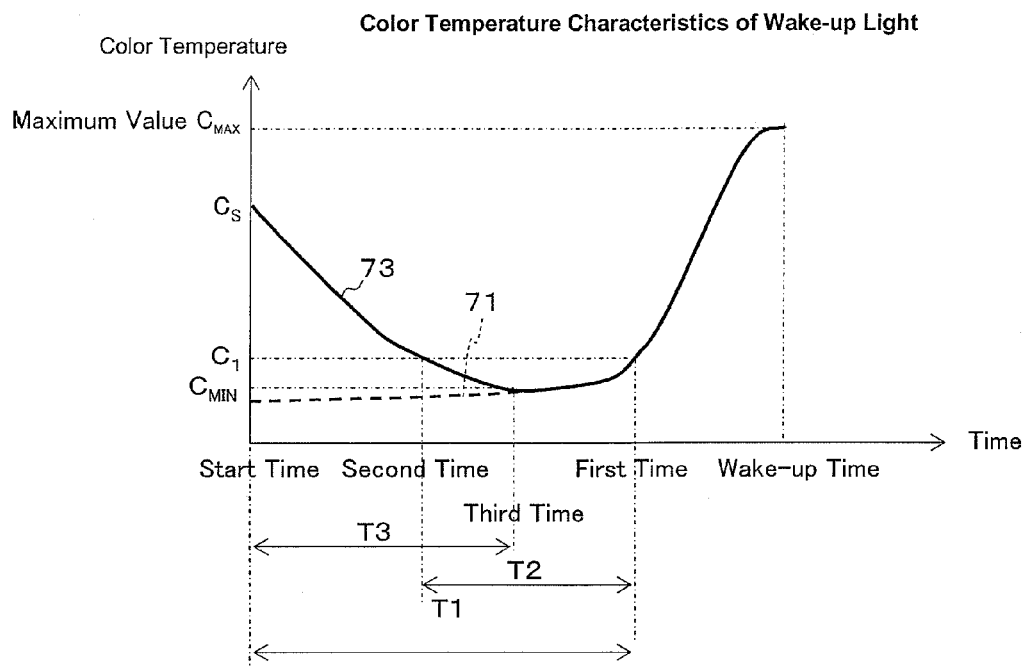
FIG. 7 is a graph showing still another example of output characteristics of the wake-up light.

Therefore, a value $C_S$ of the color temperature of the wake-up light L1 at the wake-up operation start time is set to be higher than the value $C_1$ of the color temperature of the wake-up light L1 at the first time and to be lower than the highest value $C_{MAX}$ at the maximum power time of the wake-up light L1 ($C_1 < C_S < C_{MAX}$), and the color temperature of the wake-up light L1 is gradually reduced as time go on, like the color temperature characteristics 73 shown by a solid line in FIG. 7, for example. Subsequently, the color temperature of the wake-up light L1 at the second time which is former by the second predetermined time period T2 from the first time becomes the same value as the color temperature $C_1$ of the wake-up light L1 at the first time, and the color temperature of the wake-up light L1 at the third time which is former by the third predetermined time period T3 from the first time and after the second time become the minimum value $C_{MIN}$ which is lower than the color temperature $C_1$ of the wake-up light L1 at the first time, subsequently, the color temperature of the wake-up light L1 is gradually increased toward the first time. In other words, in the color temperature characteristic 73, it is controlled such that the color temperature of the wake-up light L1 in the time period from the second time to the first time after the wake-up operation start time becomes lower than the color temperature $C_1$ of the wake-up light L1 at the first time. In addition, in case of the color temperature characteristics 71 shown by dotted line in FIG. 7 as a reference, when it is regarded that the second time is simultaneous to the wake-up operation start time, it satisfies the condition "in a time period T2 from the second time to the first time, the color temperature of the wake-up light L1 becomes lower than the color temperature $C_1$ of the wake-up light L1 at the first time".

In case of the color temperature characteristics 73, since the output of the wake-up light L1 is smaller and the color temperature of the wake-up light L1 is higher than the color temperature $C_1$ at the first time in the time period T3 from the wake-up operation start time to the third time, the wake-up light L1 contains a large amount of short wavelength ingredients which is difficult to pass through eyelid. Therefore, an amount of light which passes through the eyelid and stimulates the retina becomes fewer in comparison with the case of the color temperature characteristics 71, so that it can reduce the possibility that the user H1 awakes in the time period T3 from the wake-up operation start time to the third time. In addition, even when the user H1 awakes in the time period T3, the color temperature of the wake-up light L1 at that time is lower than the color temperature $C_{MAX}$ at the maximum power time of the wake-up light to be the highest after the first time, so that it can reduce the sense of discomfort that the user feels at the wake-up time.

Figure 8:
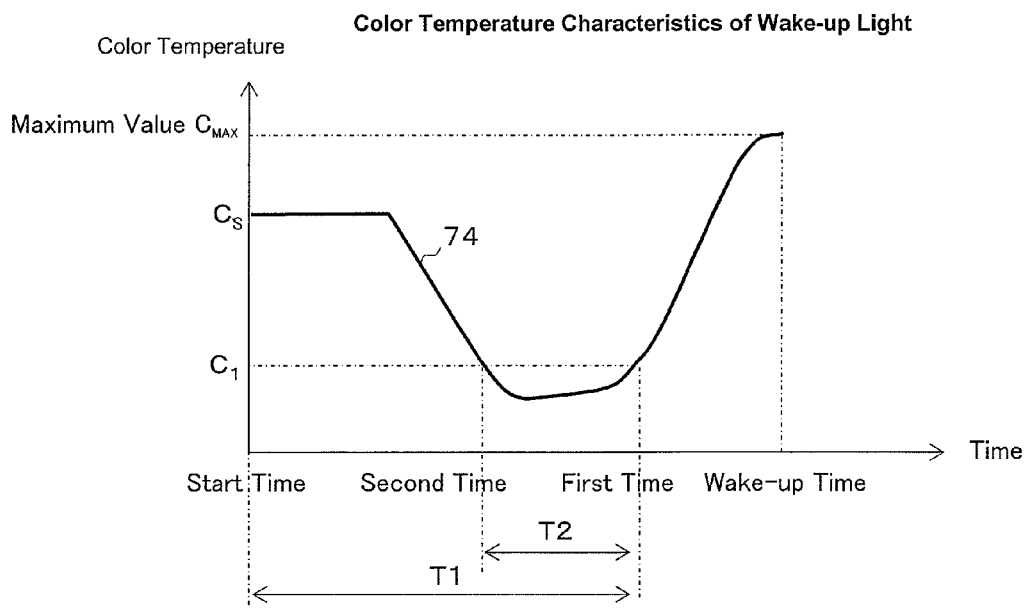
FIG. 8 is a graph showing still another example of output characteristics of the wake-up light.

In addition, it may be configured that the color temperature of the wake-up light L1 is maintained at constant at the color temperature $C_S$ at the wake-up operation start time during the predetermined time period T3 after starting the wake-up operation like the color temperature characteristics 74 shown in FIG. 8, subsequently, the color temperature of the wake-up light L1 is gradually lowered as time go on and the color temperature of the wake-up light L1 is taken the minimum value $C_{MIN}$ at the third time which is lower than the color temperature $C_1$ of the wake-up light L1 at the first time, and subsequently, the color temperature of the wake-up light L1 is gradually increased toward the first time, similar to the above mentioned color temperature characteristics 73 shown in FIG. 7. Thereby, the equivalent effects can be obtained to the case of using the color temperature 73 shown in FIG. 7.

Figure 9:
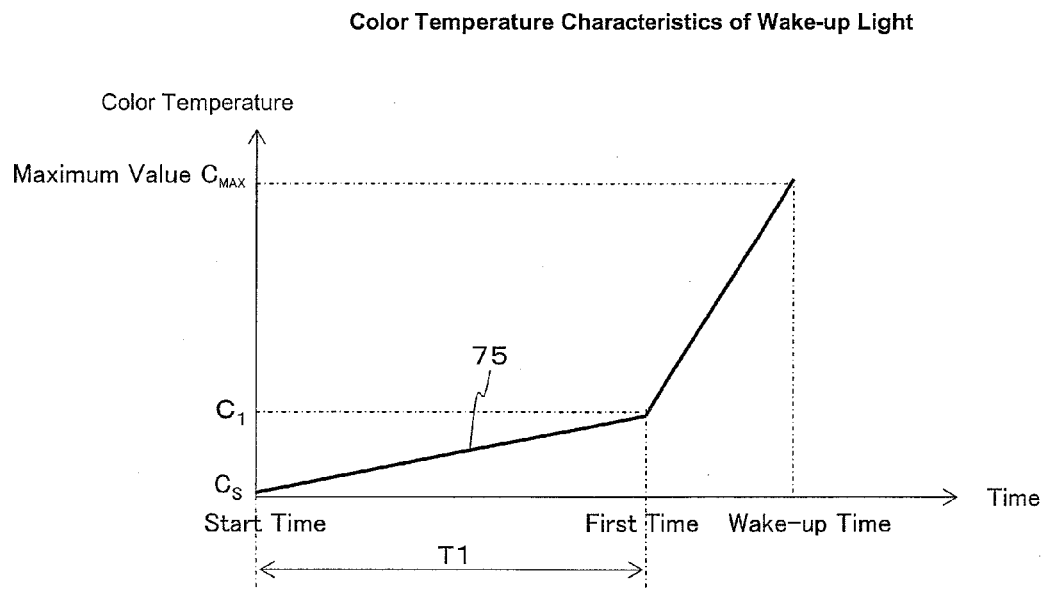
FIG. 9 is a graph showing still another example of output characteristics of the wake-up light.

Besides, the present invention is not limited to the above mentioned configurations of the embodiment, and it may be deformed in various manners corresponding to the purpose of use. For example, it may be configured that the user operates the interface apparatus 4 to input only the wake-up time, and the wake-up operation start time is automatically set on the basis of the inputted wake-up time. In addition, the output characteristics of the wake-up light L1 are not limited to those shown in FIG. 3 or FIG. 6, and it may be the characteristics increasing in an approximately constant ratio linearly. Similarly, the color temperature characteristics of the wake-up light L1 are not limited to those shown in FIG. 4, FIG. 5, FIG. 7 or FIG. 8, and it may be the characteristics increasing in an approximately constant ratio linearly like the color temperature characteristics 75 shown in FIG. 9, for example.

Figure 10:
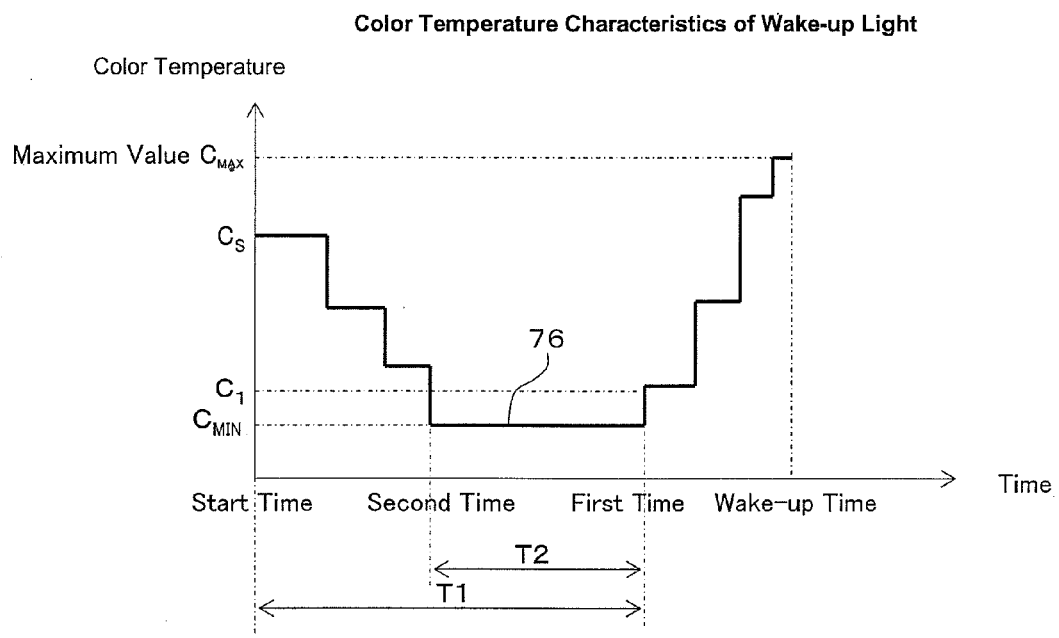
FIG. 10 is a graph showing still another example of output characteristics of the wake-up light.

Furthermore, although it is exemplified that the output and the color temperature of the wake-up light L1 irradiated from the illumination apparatus 2 are continuously, in other words, smoothly varied in the above mentioned embodiments, it may be configured to vary in discontinuous, in other words, in stages like the color temperature characteristics 76 shown in FIG. 10, for example. In addition, the illumination apparatus 2 may irradiate the wake-up light L1 on the face of the user (sleeper) H1 directly, or it may irradiate the wake-up light L1 on a wall surface or a ceiling to illuminate indirectly. Furthermore, the structure, position or positions, a number of the illumination apparatus 2 are not limited in particular.

Figure 11:
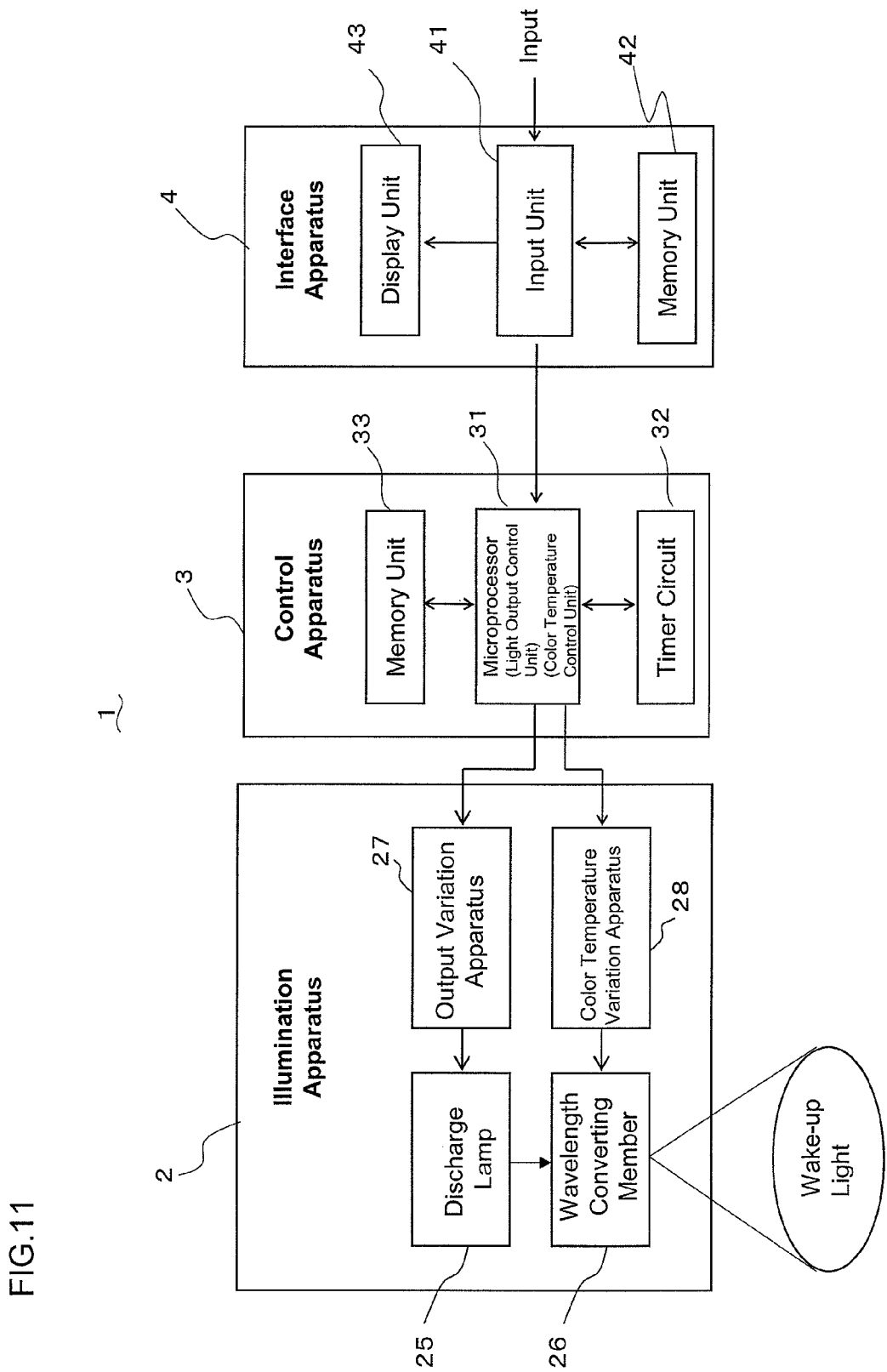
FIG. 11 is a block diagram showing a configuration of a modified example of the above mentioned wake-up system.

Still furthermore, although the illumination apparatus 2 is exemplified in the above mentioned embodiments to comprise the red light source 21, the green light source 22, the blue light source 23 and the red lighting circuit 24R, the green lighting circuit 24G and the blue lighting circuit 24B which control lighting of respective light sources 21 to 23 individually, it may be configured by a discharge lamp 25 such as a fluorescent lamp as the light source, an output variation apparatus (a discharge lamp lighting apparatus) 27 to vary the output of the wake-up light irradiated from the light source 25, and a color temperature converting apparatus 28 which drives a wavelength converting member 26 such as a dichroic filter, as shown in FIG. 11, for example. Colors of the light source which constitute the illumination apparatus 2 are not limited to red, green and blue, and it may be constituted by two colors or four colors or more, if they can realize desired color temperature. In case that the light sources 21 to 23 of the illumination apparatus 2 are configured by LEDs, organic ELs or inorganic ELs, the illumination apparatus 2 can be downsized in comparison with the case of using the discharge lamp 25 and the wavelength converting member 26 because they can be miniaturized and integrated easily.

In other words, it is sufficient that the wake-up system in accordance with the present invention comprises the illumination apparatus 2 which irradiated the wake-up light L1, and the control apparatus 3 which controls the output of the wake-up light L1 irradiated from the illumination apparatus 2, and the illumination apparatus 2 comprises an output variation apparatus 24 (the lighting circuits 24R, 24G and 24B) which varies output of the wake-up light L1 to be irradiated, and a color temperature variation apparatus 24 which varies the color temperature of the wake-up light L1, and the control apparatus 3 comprises the light output control unit (the microprocessor) 31 which controls the output variation apparatus 24 so as to increase the output of the wake-up light L1 irradiated from the illumination apparatus 2 from the wake-up operation start time to the wake-up time, and the color temperature control unit (the microprocessor) 31 which controls the color temperature variation apparatus 24 such that color temperature of the wake-up light L1 in a time period from the first time, which is a time passing the first predetermined time period T1 from the wake-up operation start time, to the wake-up becomes higher than the color temperature of the wake-up light L1 in the time period T2 from the second time, which is a time before the second predetermined time period shorter than the first predetermined time period from the first time, to the first time.

Furthermore, it is preferable that the color temperature control unit raises monotonously the color temperature of the wake-up light from the wake-up operation start time to the first time and from the first time to the wake-up time, and increases the color temperature of the wake-up light so that a rate of increase per unit time of the color temperature of the wake-up light from the first time to the wake-up time becomes larger than a rate of increase per unit time of the color temperature of the wake-up light from the wake-up operation start time to the first time.

Still furthermore, it is preferable that the color temperature control unit raises the color temperature of the wake-up light nonlinearly.

Still furthermore, it is preferable that the color temperature control unit maintains the color temperature of the wake-up light at constant from the wake-up operation start time to the first time and raises monotonously the color temperature of the wake-up light from the first time to the wake-up time.

Still furthermore, it is preferable that the color temperature control unit sets the color temperature of the wake-up light at the wake-up operation start time higher than the color temperature of the wake-up light at the first time, decreases the color temperature of the wake-up light so that the color temperature of the wake-up light at a third time between the second time and the first time is to be a minimum value lower than the color temperature of the wake-up light at the first time, and increases the color temperature of the wake-up light from the third time toward the first time.

Still furthermore, it is preferable that the color temperature of the wake-up light at the wake-up operation start time is to be a value lower than that of the color temperature of the wake-up light at the wake-up time.

Still furthermore, it is preferable that the color temperature control unit raises or falls the color temperature of the wake-up light nonlinearly.

Still furthermore, it is preferable that the light output control unit raises monotonously the output of the wake-up light from the wake-up operation start time to the first time and from the first time to the wake-up time, and increases the output of the wake-up light so that rate of increase per unit time of the output of the wake-up light from the first time to the wake-up time becomes larger than rate of increase per unit time of the output of the wake-up light from the wake-up operation start time to the first time.

Still furthermore, it is preferable that the color temperature (SIC: correctly, it should be output) control unit increases the output of the wake-up light nonlinearly.

On the other hand, it is sufficient that the control method of the illumination apparatus in accordance with the present invention is the control method of the illumination apparatus used in the wake-up system to promote wake-up of a sleeper by irradiation of wake-up light, configured to increase the output of the wake-up light irradiated from the illumination apparatus from the wake-up operation start time toward the wake-up time, and to increase the color temperature of the illumination apparatus such that the color temperature of the wake-up light in a time period from the first time, which is a time passing a first predetermined time period from the wake-up operation start time, to the wake-up becomes higher than the color temperature of the wake-up light in a time period from the second time, which is a time before a second predetermined time period shorter than the first predetermined time period from the first time, to the first time.

Furthermore, it is preferable that the color temperature of the wake-up light is raised monotonously from the wake-up operation start time to the first time and from the first time to the wake-up time, and the color temperature of the wake-up light is increased so that a rate of increase per unit time of the color temperature of the wake-up light from the first time to the wake-up time becomes larger than a rate of increase per unit time of the color temperature of the wake-up light from the wake-up operation start time to the first time.

Still furthermore, it is preferable that the color temperature of the wake-up light is raised nonlinearly.

Still furthermore, it is preferable that the color temperature of the wake-up light is maintained at constant from the wake-up operation start time to the first time and the color temperature of the wake-up light is raised monotonously from the first time to the wake-up time.

Still furthermore, it is preferable that the color temperature of the wake-up light at the wake-up operation start time is set to be higher than the color temperature of the wake-up light at the first time, the color temperature of the wake-up light is decreased so that the color temperature of the wake-up light at a third time between the second time and the first time is to be a minimum value lower than the color temperature of the wake-up light at the first time, and the color temperature of the wake-up light is increased from the third time toward the first time.

Still furthermore, it is preferable that the color temperature of the wake-up light at the wake-up operation start time is to be a value lower than that of the color temperature of the wake-up light at the wake-up time.

Still furthermore, it is preferable that the color temperature of the wake-up light is raised or fallen nonlinearly.

Still furthermore, it is preferable that the output of the wake-up light is raised from the wake-up operation start time to the first time and from the first time to the wake-up time, and the output of the wake-up light is increased so that rate of increase per unit time of the output of the wake-up light from the first time to the wake-up time becomes larger than rate of increase per unit time of the output of the wake-up light from the wake-up operation start time to the first time.

Still furthermore, it is preferable that the output of the wake-up light is increased nonlinearly.

This application is based on Japanese patent application 2009-105299, the contents of which are hereby incorporated by references of the description and drawings of the above mentioned patent application. Although the present invention has been fully described by way of example with reference to the accompanying drawings, it is to be understood that various changes and modifications will be apparent to those skilled in the art. Therefore, unless otherwise such changes and modifications depart from the scope of the present invention, they should be construed as being included therein.

The invention claimed is:

1. A wake-up system comprising:
    an illumination apparatus which irradiates wake-up light;
    a control apparatus which controls output of the wake-up light irradiated from the illumination apparatus, and
    an interface apparatus which is operated by a user to input at least a wake-up time,
    wherein the illumination apparatus comprises an output variation apparatus which varies output of the wake-up light to be irradiated, and a color temperature variation apparatus which varies color temperature of the wake-up light, and
    wherein the control apparatus comprises a light output control unit which controls the output variation apparatus so as to increase the output of the wake-up light irradiated from the illumination apparatus from a wake-up operation start time to the wake-up time input by the user, and a color temperature control unit,
    wherein time from the wake-up operation start time to the wake-up time includes in sequential order the wake-up operation start time, a second time, a first time and the wake-up time,
    wherein the first time is defined after a first predetermined time period after the wake-up operation start time,
    wherein the second time is defined before a second predetermined time period before the first time,
    wherein a remainder time period is defined from the first time to the wake-up time,
    wherein the second predetermined time period is shorter than the first predetermined time period,
    wherein the color temperature control unit controls the color temperature variation apparatus such that color temperature of the wake-up light in the remainder time period becomes higher than the color temperature of the wake-up light in the second predetermined time period, and
    wherein the color temperature control unit raises monotonously the color temperature of the wake-up light from the wake-up operation start time to the first time and from the first time to the wake-up time input by the user, and increases the color temperature of the wake-up light so that a rate of increase per unit time of the color temperature of the wake-up light from the first time to the wake-up time becomes larger than a rate of increase per unit time of the color temperature of the wake-up light from the wake-up operation start time to the first time.

2. The wake-up system in accordance with claim 1, characterized by that the color temperature control unit raises the color temperature of the wake-up light nonlinearly.

3. The wake-up system in accordance with claim 1, characterized by that the color temperature of the wake-up light at the wake-up operation start time is to be a value lower than that of the color temperature of the wake-up light at the wake-up time.

4. The wake-up system in accordance with claim 1, characterized by that the color temperature control unit raises or lowers the color temperature of the wake-up light nonlinearly.

5. The wake-up system in accordance with claim 1, characterized by that the light output control unit raises monotonously the output of the wake-up light from the wake-up operation start time to the first time and from the first time to the wake-up time, and increases the output of the wake-up light so that rate of increase per unit time of the output of the wake-up light from the first time to the wake-up time becomes larger than rate of increase per unit time of the output of the wake-up light from the wake-up operation start time to the first time.

6. The wake-up system in accordance with claim 5, characterized by that the light output control unit nonlinearly increases the output of the wake-up light.

7. The wake-up system in accordance with claim 1,
    wherein the color temperature of the wake-up light is at a maximum value at the wake-up time.

8. The wake-up system in accordance with claim 1,
    wherein the color temperature of the wake-up light reaches a maximum value at the wake-up time.

9. A control method of an illumination apparatus used in a wake-up system to promote wake-up of a sleeper by irradiation of wake-up light, the method comprising:
    increasing output of the wake-up light irradiated from the illumination apparatus from a wake-up operation start time toward a wake-up time input by a user, and
    increasing color temperature of the illumination apparatus,
    wherein time from the wake-up operation start time to the wake-up time includes in sequential order the wake-up operation start time, a second time, a first time and the wake-up time,
    wherein the first time is defined after a first predetermined time period from the wake-up operation start time,
    wherein the second time is defined before a second predetermined time period before the first time,
    wherein a remainder time period is defined from the first time to the wake-up time, wherein the second predetermined time period is shorter than the first predetermined time period,
    wherein the color temperature is increased such that color temperature of the wake-up light in the remainder time period becomes higher than the color temperature of the wake-up light in the second predetermined time period, and
    wherein the color temperature of the wake-up light is raised monotonously from the wake-up operation start time to the first time and from the first time to the wake-up time input by the user, and the color temperature of the wake-up light is increased so that a rate of increase per unit time of the color temperature of the wake-up light from the first time to the wake-up time becomes larger than a rate of increase per unit time of the color temperature of the wake-up light from the wake-up operation start time to the first time.

10. The control method of the illumination apparatus in accordance with claim 9, characterized by that the color temperature of the wake-up light is raised nonlinearly.

11. The control method of the illumination apparatus in accordance with claim 9, characterized by that the color temperature of the wake-up light at the wake-up operation start time is to be a value lower than that of the color temperature of the wake-up light at the wake-up time.

12. The control method of the illumination apparatus in accordance with claim 9, characterized by that the color temperature of the wake-up light is raised or lowered nonlinearly.

13. The control method of the illumination apparatus in accordance with claim 9, characterized by that the output of the wake-up light is raised from the wake-up operation start time to the first time and from the first time to the wake-up time, and the output of the wake-up light is increased so that rate of increase per unit time of the output of the wake-up light from the first time to the wake-up time becomes larger than rate of increase per unit time of the output of the wake-up light from the wake-up operation start time to the first time.

14. The control method of the illumination apparatus in accordance with claim 13, characterized by that the output of the wake-up light is increased nonlinearly.

15. The control method of the illumination apparatus in accordance with claim 10,
   wherein the color temperature of the wake-up light is at a maximum value at the wake-up time.

16. The control method of the illumination apparatus in accordance with claim 9,
   wherein the color temperature of the wake-up light reaches a maximum value at the wake-up time.

* * * * *